(12) United States Patent
Crouch

(10) Patent No.: US 9,044,173 B2
(45) Date of Patent: Jun. 2, 2015

(54) IMPLANTED DEVICE X-RAY RECOGNITION AND ALERT SYSTEM (ID-XRAS)

(71) Applicant: Eron D Crouch, Corsicana, TX (US)

(72) Inventor: Eron D Crouch, Corsicana, TX (US)

(*) Notice: Subject to any disclaimer, the term of this patent is extended or adjusted under 35 U.S.C. 154(b) by 268 days.

(21) Appl. No.: 13/657,874

(22) Filed: Oct. 23, 2012

(65) Prior Publication Data

US 2014/0112567 A1    Apr. 24, 2014

(51) Int. Cl.
| | |
|---|---|
| G06K 9/00 | (2006.01) |
| A61B 6/12 | (2006.01) |
| G06T 7/00 | (2006.01) |
| A61B 6/00 | (2006.01) |
| G06F 19/00 | (2011.01) |

(52) U.S. Cl.
CPC ............... *A61B 6/12* (2013.01); *A61B 6/5217* (2013.01); *A61B 6/563* (2013.01); *G06F 19/321* (2013.01); *G06T 7/0014* (2013.01); *G06T 2207/30004* (2013.01)

(58) Field of Classification Search
USPC .................................................. 382/128–134
See application file for complete search history.

(56) References Cited

U.S. PATENT DOCUMENTS

| 7,885,441 | B2* | 2/2011 | Node-Langlois et al. ..... 382/128 |
| 2005/0025347 | A1* | 2/2005 | Makram-Ebeid et al. ..... 382/128 |
| 2005/0147283 | A1* | 7/2005 | Dwyer et al. ................. 382/128 |
| 2005/0192495 | A1* | 9/2005 | Makram-Ebeid et al. ..... 600/407 |
| 2010/0135553 | A1* | 6/2010 | Joglekar ....................... 382/128 |
| 2011/0087465 | A1* | 4/2011 | Mahfouz ........................... 703/1 |
| 2012/0015316 | A1* | 1/2012 | Sachdeva et al. ............... 433/24 |
| 2012/0106819 | A1* | 5/2012 | Fernandez Oca ............ 382/132 |

\* cited by examiner

*Primary Examiner* — Alex Liew

(57) ABSTRACT

This system comprises a method and software application that, when used in conjunction with digital radiographic imaging software, automatically locates and identifies surgically-implanted devices located inside of a patient and instantly notifies the healthcare provider viewing the digital radiographic image of clinically pertinent information regarding the device, such as, but not limited to the manufacturer, model, and manufacturer notifications, alerts, and/or recalls. In the case of pacemakers and defibrillators, this system also identifies defects in pacemaker and/or defibrillator leads.

3 Claims, 5 Drawing Sheets

ID-XRAS:

ID-XRAS Database    Unknown Surgically-Implanted Device

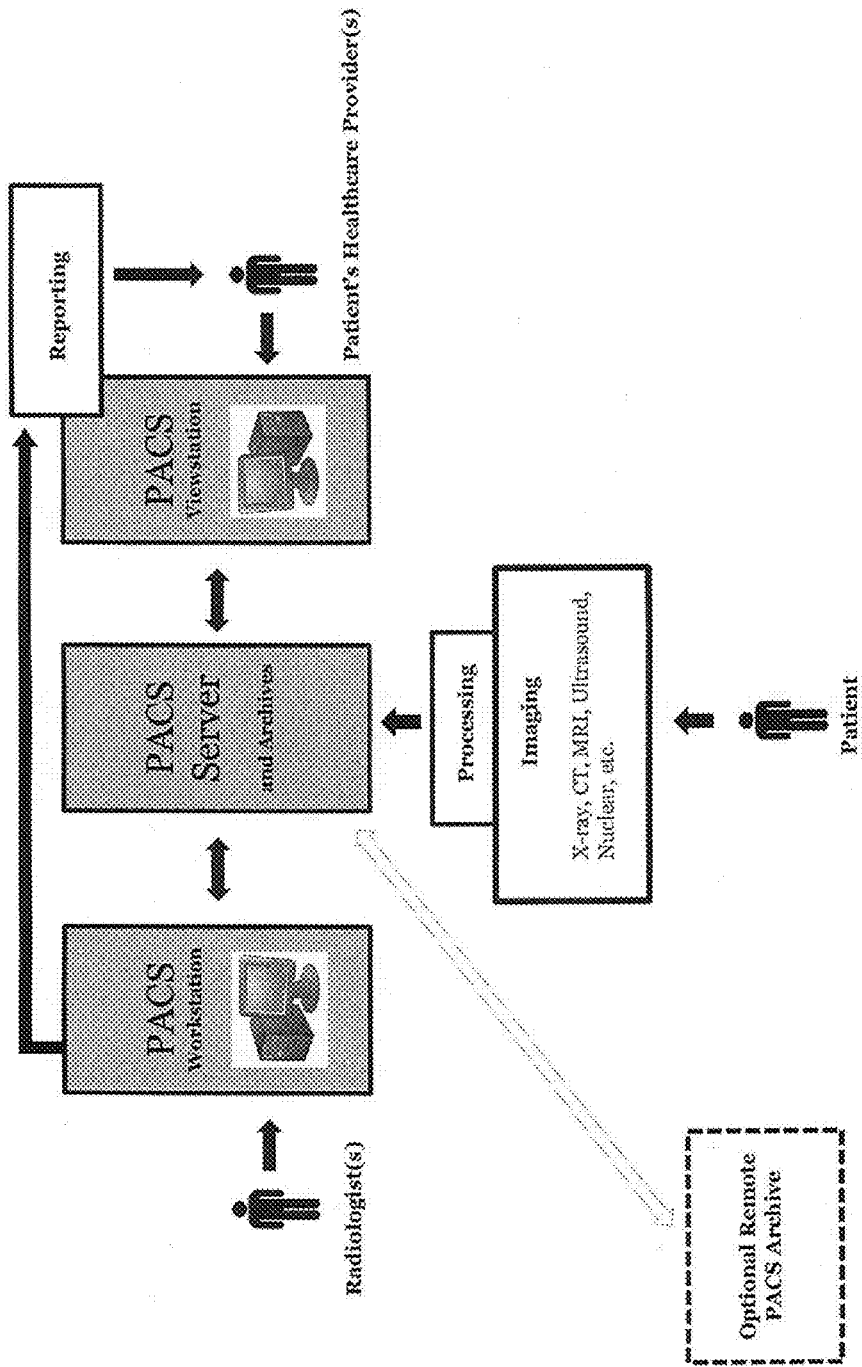

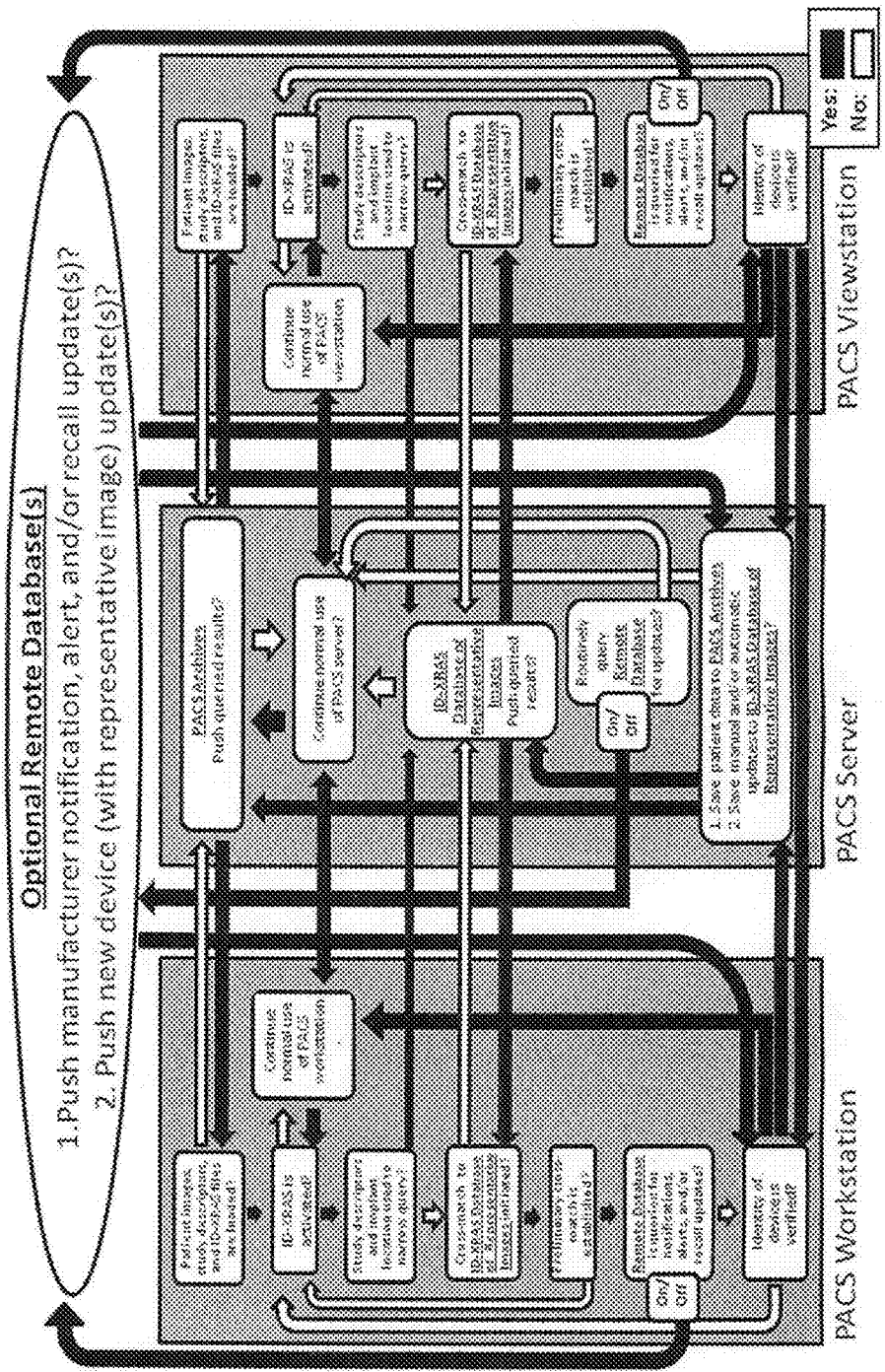

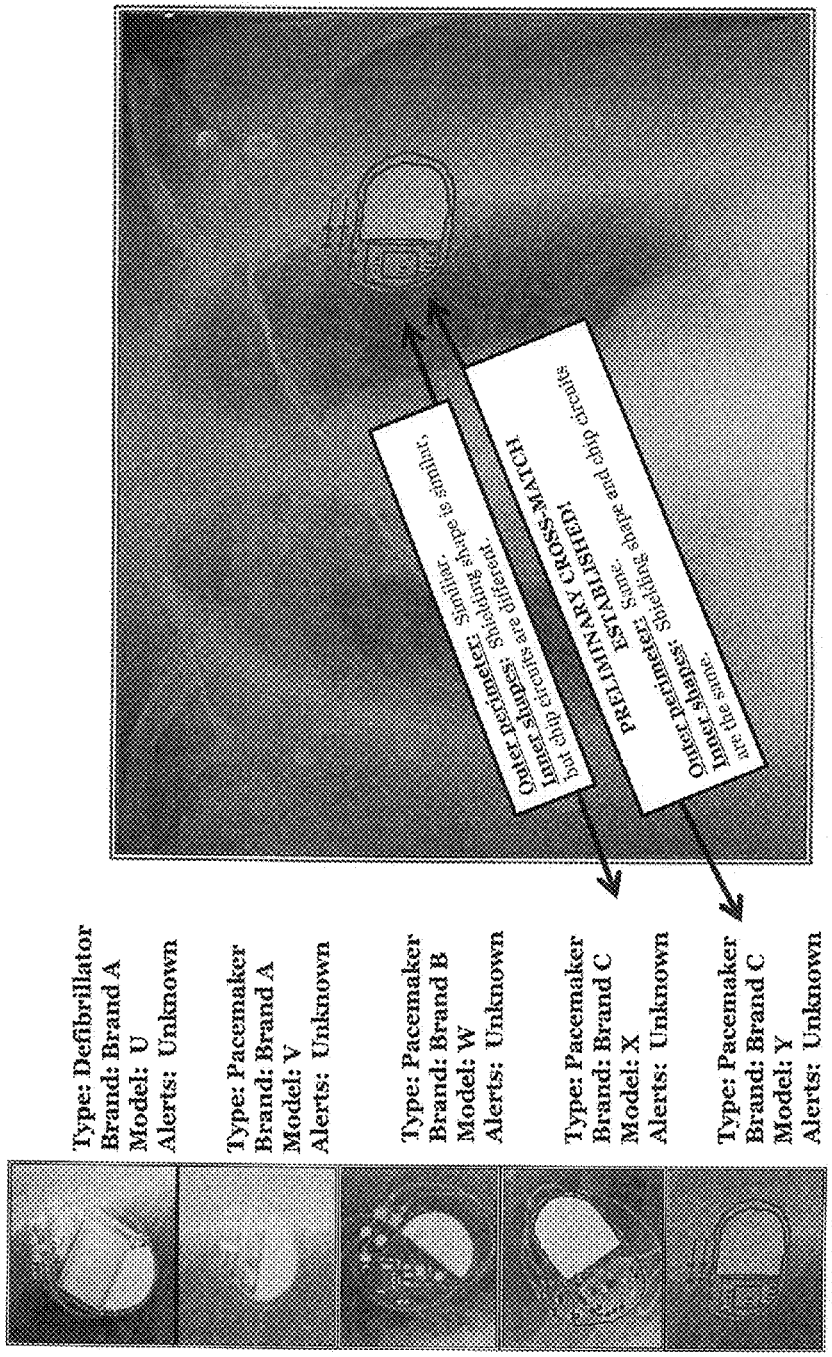

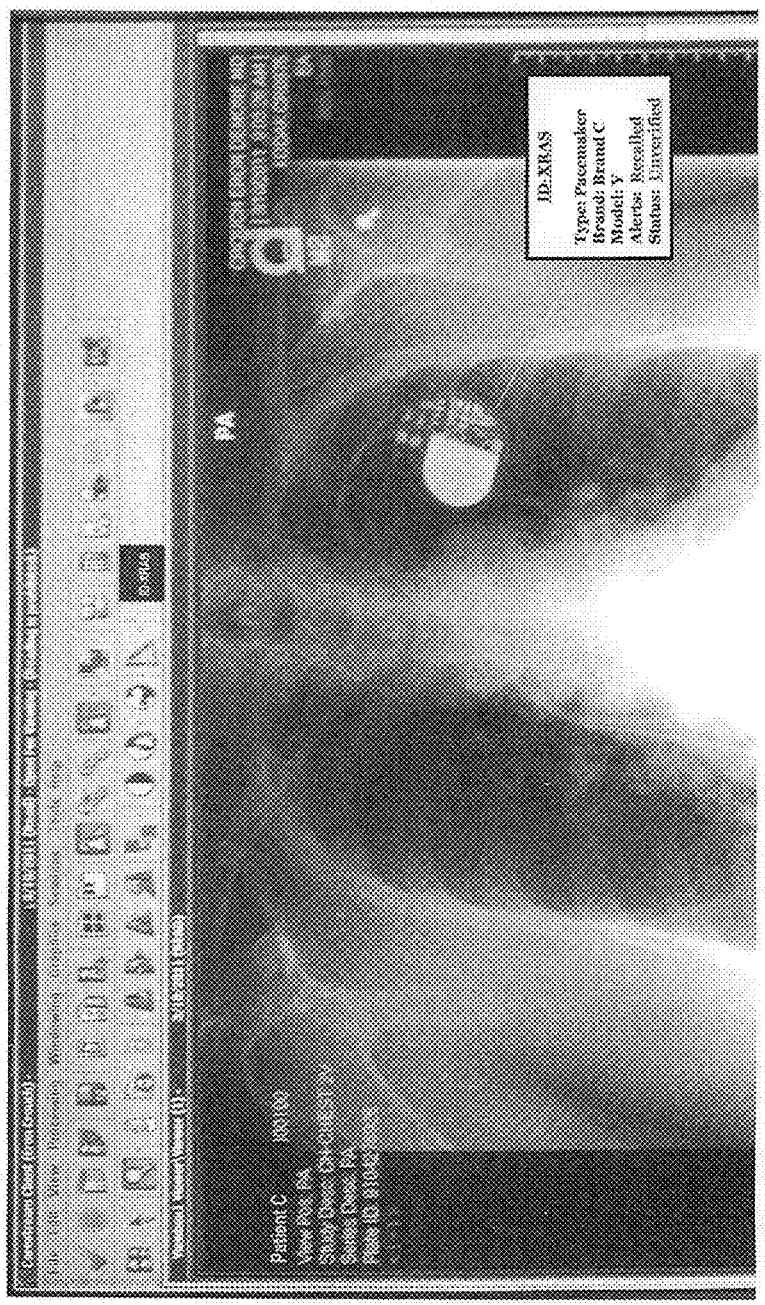
ID-XRAS: Figure 4

ID-XRAS: Figure 5

*Optional, automated, ID-XRAS notifications in the report header.*

---

EXAMPLE REGIONAL HOSPITAL

Patient Name: Patient C
Report Date: 10-Mar-2011 08:59
Description: Chest x-ray (AP projection)

Reason For Study: Pacemaker identification.
Implanted Device(s):
    Manufacturer: Brand C (1-800-555-5555)
    Type: Pacemaker
    Model: Y
    Status: Verified
    Alerts: Recall alert at:
http://www.accessdata.fda.gov/scripts/cdrh/cfdocs/cfRES/xxxxxx1xxxxxx.

Findings: There is no evidence of cardiopulmonary pathology. A dual-chamber pacemaker is visualized. Please see pacemaker recall notification listed above.

US 9,044,173 B2

IMPLANTED DEVICE X-RAY RECOGNITION AND ALERT SYSTEM (ID-XRAS)

CROSS REFERENCE TO RELATED APPLICATIONS

This nonprovisional relates to provisional application No. 61/550,405 filed on Oct. 23, 2011.

STATEMENT REGARDING FEDERALLY SPONSORED RESEARCH OR DEVELOPMENT

Not Applicable

BACKGROUND OF THE INVENTION

The present embodiments relate to medical imaging. In particular, automated identification of surgically implanted devices, including brand and model, with subsequent automated identification of manufacturer notifications, alerts, and/or recalls related to said identified devices, with subsequent automated notification of the healthcare provider viewing said medical image. One type of medical imaging is x-ray.

BRIEF SUMMARY OF THE INVENTION

Over the past two decades, the majority of hospitals and/or health care systems have replaced analog radiographic imaging with electronic, picture archiving and communications systems (PACS). A PACS is a network of computers used by radiology departments that replaces film with electronically stored and displayed digital images. It provides archives for storing multimodality images (i.e. x-rays, CT scans, and MRIs). It integrates images with patient demographic information, facilitates laser printing of images, and displays both images and patient information at work stations throughout the network. It also allows viewing of images in remote locations. These powerful PACS networks place the archived images of an entire radiology department at the fingertips of any healthcare provider with secured internet access or access to an onsite workstation.

Currently, there are millions of people in the world with surgically-implanted devices. These surgically implanted devices include, but are not limited to, artificial hearts, automatic implantable cardiac defibrillators (AICD) and leads, bone fusion stimulators, cochlear implants, cosmetic implants, cranial plates/screws, dental implants and/or hardware, fracture plates/screws, heart valves, hip joint replacements, implantable pain pumps, knee joint replacements, metallic TMJ implants, nerve stimulators, oral surgery implants, pacemakers and leads, Parkinson's control systems, penile implants, podiatry plates/screws, shoulder joint replacements, spinal cord stimulators, spinal implants/plates/screws/rods/cages, and ventricular assist devices.

Many times it is important to rapidly identify and access critical information regarding these devices—especially information regarding manufacturer warnings or recalls of the device. Surgically-implanted devices are routinely seen by PACS. The most common modality of digital imaging is x-ray, and serendipitously happens to be the optimal modality for viewing most surgically-implanted devices. Sometimes, when the surgically-implanted device is not the question at hand, the details of these devices are unfortunately overlooked by busy healthcare providers. Other times, when the information is actually being sought, healthcare providers are usually able to identify the type of device (i.e. "This is a pacemaker."), but find it difficult to keep up with more specific, yet critical information, such as manufacturer, model, and recall information by simply viewing the device by x-ray. Sometimes, this information is essential in determining whether a surgically-implanted device should be physically or electronically adjusted, surgically extracted, or replaced. Other times, this information allows healthcare providers to contact the correct manufacturer for guidance or assistance. Currently, patients are given an identification card at the time of surgery and advised to keep this information with them at all times. For many different reasons, patients often find themselves in an emergent situation without this identification card and unfortunately place themselves and their healthcare provider in a compromised position. As the number of surgically-implanted devices and hardware continues to increase, healthcare organizations and providers will face increasing challenges in correctly identifying these devices, in terms of patient outcomes, as well as legal liability (FIG. 1).

The proposed art addresses this emerging problem using the following method (FIG. 2): The surgically-implanted device is detected and identified by software that uses an automatically-updated, known database of representative images of surgically-implanted devices. Although they are not images of the patient's actual device, the software uses these representative images to match the unique shapes of the outer perimeter and/or the unique shapes and/or spatial resolution of the inner components of the patient's medically-implanted device. These unique outer and inner components are made visible by x-ray (FIG. 3). Once the manufacturer and model of the medically-implanted device is recognized, this information is digitally displayed on the screen. Subsequently, an automatic query of a known internet-based database is made to identify any recalls of the identified device. Last, any discovered recalls are digitally displayed on the screen as well (FIG. 4).

BRIEF DESCRIPTION OF THE SEVERAL VIEWS OF DRAWINGS

FIG. 1: The architecture of a typical PACS.

FIG. 2: A master flow chart outlining the method used by the ID-XRAS to interact with the typical PACS hardware and software.

FIG. 3: An illustrative diagram depicting ID-XRAS cross-matching of unique shapes of the outer perimeter and/or the unique shapes and/or spatial resolution of the inner components of a typical surgically-implanted device with the database of known representative images, as viewed by x-ray, for the purpose of establishing a preliminary identification of the surgically-implanted device.

FIG. 4: An illustration of a typical PACS radiographic image workstation or viewstation, with an integrated illustration of ID-XRAS displaying a label on the preliminarily-identified, surgically-implanted device.

FIG. 5: An illustration of a typical radiologist's report header that has been generated using PACS demographic information, and demonstrating the optional, automatic, incorporation of the ID-XRAS findings within the report header.

DETAILED DESCRIPTION OF THE INVENTION

Over the past two decades, the majority of hospitals and/or health care systems have replaced analog radiographic imaging with electronic, picture archiving and communications systems (PACS). A PACS is a network of computers used by radiology departments that replaces film with electronically stored and displayed digital images. It provides archives for storing multimodality images (i.e. x-rays, CT scans, and MRIs). It integrates images with patient demographic information, facilitates laser printing of images, and displays both images and patient information at work stations throughout the network. It also allows viewing of images in remote locations. These powerful PACS networks place the archived images of an entire radiology department at the fingertips of any healthcare provider with secure internet access privileges or access to an onsite workstation (FIG. 1).

Currently, there are millions of people in the world with surgically-implanted devices. These surgically-implanted devices include, but are not limited to, artificial hearts, automatic implantable cardiac defibrillators (AICD), bone fusion stimulators, cochlear implants, cosmetic implants, cranial plates/screws, dental implants and/or hardware, fracture plates/screws, hip joint replacements, implantable pain pumps, knee joint replacements, metallic TMJ implants, nerve stimulators, oral surgery implants, pacemakers, Parkinson's control systems, penile implants, podiatry plates/screws, shoulder joint replacements, prosthetic heart valves, spinal cord stimulators, spinal implants/plates/screws/rods/cages, and ventricular assist devices.

Many times, it is important to rapidly identify and access critical information regarding these devices—especially information regarding manufacturer notifications, alerts, and/or recalls of the device. Surgically-implanted devices are routinely seen by PACS. The most common modality of digital imaging is x-ray, and serendipitously happens to be the optimal modality for viewing a variety of surgically-implanted devices. Sometimes, when the surgically-implanted device is not the question at hand, the details of these devices are unfortunately overlooked by busy healthcare providers. Other times, when the information is actually being sought, healthcare providers are usually able to identify the type of device (i.e. "This is a pacemaker."), but find it difficult to keep up with more specific, yet critical information, such as manufacturer, model, manufacturer notifications, alerts, and/or recalls, by simply viewing the device by x-ray. Sometimes, this information is essential in determining whether a surgically-implanted device should be physically or electronically adjusted, surgically extracted, or replaced. Other times, this information allows healthcare providers to contact the correct manufacturer for guidance or assistance. Currently, patients are given an identification card at the time of surgery and advised to keep this information with them at all times. For many different reasons, patients often find themselves in an emergent situation without this identification card and unfortunately place themselves and their healthcare provider in a compromised position. As the number of surgically-implanted devices and hardware continues to increase, healthcare organizations and providers will face increasing challenges in correctly identifying these devices, in terms of patient outcomes, as well as legal liability.

The disclosures made herein relate to methods and equipment, in the form of computer software, that when used in conjunction with the typical PACS server, workstation, and/or viewstation, automatically and electronically identifies, surgically-implanted devices located inside of a patient and instantly notifies the healthcare provider viewing the digital radiographic image of clinically pertinent information regarding the device, such as, but not limited to the manufacturer, model, and manufacturer notifications, alerts, and/or recalls. Such methods and equipment, which are in accordance with embodiments of the disclosures made herein, are adapted to overcome limitations associated with the forementioned conventional methods and equipment. The embodiment of the disclosures made herein is hereafter referred to as an x-ray recognition and alert system for implanted devices (ID-XRAS).

Moving now to the accompanying FIG. 2, this master flowchart provides an overview of the method used by the ID-XRAS to electronically and automatically, identify surgically-implanted devices and subsequently provide manufacturer notifications, alerts, and/or recalls. First, if a radiographic image is viewed by a healthcare provider and appears to have an unknown surgically-implanted device, the ID-XRAS provides a method to trigger activation. One embodiments of this trigger could be a computer icon, herein upon being manually selected, results in a specialized cursor that is manually positioned over the unknown surgically-implanted device. An embodiment of this specialized cursor could be an adjustable oval that encompasses the boundaries of the device in question. This step defines the image to be identified by the ID-XRAS. Once the specialized cursor is in position, the computer icon could be selected a second time, thus activating the automatic ID-XRAS database querying and/or cross-matching process.

It is customary for the typical PACS to provide descriptors, such as the type of image (i.e. x-ray, CT scan, MRI) and body part depicted by the image (i.e. head, chest, hip). If available, the ID-XRAS could at this time use these descriptors to narrow the search criteria used for the impending query of the ID-XRAS database of representative images. If descriptors are not available, the entire ID-XRAS database of representative images is queried, in an attempt to establish a preliminary cross-match.

Before moving to the process of establishing a preliminary cross-match, let us describe the content and functions of the ID-XRAS database of representative images. The ID-XRAS provides a comprehensive database of representative images of surgically-implanted devices. This database of representative images can be located locally (i.e. computer hard drive or onsite PACS server) or remotely (i.e. via the internet or independently owned remote server). The embodiment in FIG. 2 positions this database of representative images in the PACS server. Each representative image is labeled and/or categorized by type, manufacturer, and model. Each representative image is also labeled with descriptors, such as the type of image and body part depicted by the image. Likewise, each type, manufacturer, and model of surgically-implanted device in the database is pre-labeled with all known manufacturer notifications, alerts, and/or recalls of said device at the time of software production. Furthermore, the ID-XRAS provides a means by which said information regarding manufacturer notifications, alerts, and/or recalls can be remotely and automatically updated, in real-time, while operational within the PACS. The embodiments in FIG. 2 outline two distinct processes by which ID-XRAS updates of the ID-XRAS database of representative images: a) After being queried by a PACS workstation or viewstation, an update of manufacturer notifications, alerts, and/or recalls for a given surgically-implanted device is retrieved from a remote database. This update is ultimately saved to the PACS server. During this process, all new updates regarding new types, manufacturers, and models of surgically-implanted devices, as well as all new updates of manufacturer notifications, alerts, and/or recalls could be retrieved from the remote database and also saved to the PACS server for future use, if information regarding previous update received by the PACS server was provided to the remote database by the PACS workstation or viewstation via the PACS server at the time of the query; and b) From time to time, in a pre-determined fashion, a remote database is automatically and/or manually queried for new updates by the PACS server. During this process, information regarding previous updates received by the PACS server is provided to the remote database, and all new updates regarding new types, manufacturers, and models of surgically-implanted devices, as well as all new updates of manufacturer notifications, alerts, and/or recalls are retrieved from the remote database and saved to the PACS server for future use.

We now move to the process of establishing a preliminary cross-match between the unknown surgically-implanted device and a ID-XRAS representative image. Although the images in the database are not images of the patient's actual device, the ID-XRAS uses these representative images, made visible by digital radiographic imaging, to create an accurate cross-match to the unique shapes of the outer perimeter and/or the unique shapes and/or spatial orientation of the inner components of the patient's actual device. In FIG. 3, the diagram represents the use of unique shapes of the outer perimeter and/or the unique shapes and/or spatial orientation of the inner components of the patient's unknown surgically-implanted devices to accurately cross-match the device to a known image in an ID-XRAS database of representative images. The image on the right, labeled "Unknown Surgically-Implanted Device", is a digital chest x-ray, taken from a patient, located within a PACS. The outlined area of interest reveals an unknown surgically-implanted device which resembles a pacemaker. The images on the right, labeled "ID-XRAS Database", displays representative digital x-ray images of pacemakers and defibrillators from three major manufacturers and are labeled Brand A; Brand B; and Brand C. The fourth and fifth representative digital x-ray images, labeled Brand C, model X and Brand C, model Y illustrate that the same manufacturer sometimes has more than one model of device. The bold lines outline the unique shapes of the outer perimeter and/or the unique shapes and/or spatial orientation of the inner components that could be used by an object recognition algorithm to differentiate devices—in this case Brand C, model X; and Brand C, model Y. The final image below demonstrates a cross-match of unique shapes of the outer perimeter and/or the unique shapes and/or spatial orientation of the inner components between the patient's unknown surgically-implanted device and a representative image from the ID-XRAS database, which is known to be a pacemaker Brand C, model Y. As a result, the patient's unknown surgically-implanted device is identified as pacemaker Brand C, model Y.

Once a preliminary cross-match between the patient's unknown surgically-implanted device and a representative image from the ID-XRAS database of representative images is established, the manufacturer and model of the surgically-implanted device is preliminarily identified. This information can be digitally displayed on the screen. One embodiment of preliminarily displaying the manufacturer and model of the surgically-implanted device on the screen would be in the form a digital label stemming from the digital image of the surgically-implanted device. Next, the ID-XRAS queries a remote database, via the internet, to search for notifications, alerts, and/or recalls associated with the preliminarily-identified surgically-implanted device. The queried results are then retrieved by the requesting workstation or viewstation. Any discovered notifications, alerts, and/or recalls could also be digitally displayed on the screen, of which one embodiment would be the fore-mentioned digital label stemming from the digital image of the surgically-implanted device (FIG. 4).

At this point, the ID-XRAS provides a method(s) of verifying the identity of the preliminarily-identified surgically-implanted device. Many methods of verification are possible; therefore, the three embodiments described are not meant to be limiting in the scope and/or spirit of the disclosure. One embodiment for verifying the identity of the preliminary-identified surgically-implanted device could be in the form of a software application asking the healthcare provider a pointed question(s) that assist the software in narrowing the list of possibilities from the ID-XRAS database of representative images (example: This is a pacemaker, Brand C. It is either a Model X, Model Y. Do you see the characters X123 or Y123 located beneath the battery? Y123. This is, indeed, a pacemaker Brand C, Model Y). These questions, of course, would have to be specific to each device and would be beyond the scope of this document to list every question individually. As commercial and government patient registries of surgically-implanted devices emerge, it is foreseeable that a second embodiment for verifying the identity of the preliminary-identified surgically-implanted device could be an automated query of an internet-based, commercial or government registry of surgically-implanted devices, including or not including manufacturer notifications, alerts, and/or recalls, to look for registration of the patient's actual surgically-implanted device. It is also foreseeable that, in this scenario, if the patient's registration information was not located in the registry or was erroneous, the results of the above-mentioned cross-match could be used to alert the commercial or governmental registry of the missing or erroneous file. A third embodiment for verifying the identity of the preliminary-identified, surgically-implanted device could be in the form of a digital signature from an authorized healthcare provider (i.e. the ordering physician or interpreting radiologist), vouching that the device is correctly identified, after reviewing the appropriate medical records and/or any other reliable source at a later point in time. Once verified, the verified status could also be digitally displayed on the screen, of which one embodiment would be the fore-mentioned digital label stemming from the digital image of the surgically-implanted device.

At this point, the ID-XRAS provides the ability to save the fore-mentioned, verified surgically-implanted device information, including or not including manufacturer notifications, alerts, and/or recalls, to the PACS server for the purpose of: a) archiving this information in the PACS, as an attachment to the image of origin, for future viewing of the same image in the same patient; b) referencing this information to past, present, and/or future occurrences of the same surgically-implanted device on different radiographic images of the same patient; c) updating the ID-XRAS database of representative images when a new, verified surgically-implanted device and/or a newly-discovered notification, alert, and/or recall is not already found in the fore-mentioned ID-XRAS database of representative images. It is worth noting that while it may be a feasible embodiment to allow healthcare providers located at either PACS viewstations or PACS workstations to save verified surgically-implanted device information, including manufacturer notifications, alerts, and/or recalls, to the PACS server, some system administrators may optionally reserve this function for PACS workstations only. Both options are represented in FIG. 2.

Following through to the next use of the PACS, by either a PACS workstation or viewstation, the FIG. 2 master flow chart outlines how newly-saved, verified, surgically-implanted device information, including notifications, alerts, and/or manufacturer recalls, to the PACS server would then be incorporated with the next manual activation of the ID-XRAS. It is also worth noting that an optional embodiment, which is also represented in FIG. 2, could be to "turn off" the PACS workstation and/or PACS viewstation function(s) to query a remote database and "turn on" the PACS server function to routinely and/or periodically query a remote database, then save newly-reported, surgically-implanted device information, including notifications, alerts, and/or manufacturer recalls, to the PACS server, to be incorporated with the next manual activation of the ID-XRAS. Furthermore, newly-saved, verified, surgically-implanted device information, including notifications, alerts, and/or manufacturer recalls, could optionally be automatically incorporated into the header of the official report from the radiologist (FIG. 5).

In the preceding detailed, written description of the invention, reference has been made to the accompanying figures, which illustrate methods and specific embodiments in which the invention may be practiced. These methods and embodiments have been described in sufficient detail to enable those skilled in the art to practice the invention. It is to be understood that other suitable embodiments may be utilized and that logical changes may be made without departing from the spirit or scope of the invention. To avoid unnecessary detail, the descriptions omit certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the invention.

The invention claimed is:

1. A computer program, stored in a non-transitory computer readable medium executed by a computer processor, comprising:

identifying the identity of an unknown previously surgically-implanted device located in a radiographic digital image by recognizing radio-opaque symbols, lettering and/or numbers, unique shapes of the outer perimeter and/or the spatial orientation of the inner components of said surgically-implanted device;

digitally labeling the digital image of a surgically-implanted device located in a digital radiographic image viewer by type, brand, make and model, so that said surgically-implanted device is now permanently identified within the radiographic digital image viewer by digital label; and continuously updating the digital label of a digital image of a surgically-implanted device located in a digital radiographic image viewer with alerts of clinically relevant information authorized by end users, wherein said digital labels include at least one of the following such as manufacturer notifications, warnings, recall information regarding the identified device or customizable information.

2. The computer program of claim 1 wherein: said surgically-implanted devices at least one of the following: artificial hearts, automatic implantable cardiac defibrillators (AICD) and leads bladder stimulation devices, bone fusion stimulators, cochlear implants, cosmetic implants, cranial plates/screw, dental implants and/or hardware, fracture plates/screws, heart valves, hip joint replacements, implantable pain pumps, knee joint replacements, metallic TMJ implants, nerve stimulators, oral surgery Implants, pacemakers and leads, Parkinson's control systems, penile implants, podiatry plates/screws, shoulder joint replacements, spinal cord stimulators, spinal implants/plates/screws/rods/cages, and ventricular assist devices.

3. The computer program of claim 1 also includes: digitally labeling and continuously updating the past, present and future occurrences of the same surgically-implanted device within the PACS.

\* \* \* \* \*